United States Patent

Gethöffer et al.

[11] Patent Number: 5,994,284
[45] Date of Patent: Nov. 30, 1999

[54] IMIDOPEROXYCARBOXYLIC ACIDS, THEIR USE IN DETERGENTS AND CLEANING AGENTS

[75] Inventors: Hanspeter Gethöffer, Frankfurt am Main; Gerd Reinhardt, Kelkheim, both of Germany

[73] Assignee: Clariant GmbH, Frankfurt am Main, Germany

[21] Appl. No.: 08/728,533

[22] Filed: Oct. 9, 1996

Related U.S. Application Data

[63] Continuation of application No. 08/456,293, May 31, 1995, abandoned, which is a continuation of application No. 07/746,929, Aug. 19, 1991, abandoned, which is a continuation of application No. 07/376,000, Jul. 6, 1989, Pat. No. 5,061,807.

[30] Foreign Application Priority Data

Jul. 8, 1988 [DE] Germany .............................. 38 23 172

[51] Int. Cl.⁶ ..................................................... D06L 3/00
[52] U.S. Cl. .......................... 510/316; 510/309; 510/310; 510/313; 252/186.42; 548/473
[58] Field of Search ............................ 548/473; 568/479, 568/588; 510/316, 309, 310, 313; 252/186.42

[56] References Cited

U.S. PATENT DOCUMENTS

| | | | |
|---|---|---|---|
| 3,712,907 | 1/1973 | Glich et al. | 548/479 |
| 3,931,224 | 1/1976 | Santa et al. | 548/473 |
| 4,376,218 | 3/1983 | Izzard et al. | 568/559 |
| 4,385,008 | 5/1983 | Hignett | 260/502 R |
| 4,403,994 | 9/1983 | Hignett | 8/111 |
| 4,483,781 | 11/1984 | Hartman | 252/174 |
| 4,536,313 | 8/1985 | Hignett et al. | 252/100 |
| 4,547,451 | 10/1985 | Jasne et al. | 430/215 |
| 4,604,409 | 8/1986 | Gagliani et al. | 521/163 |
| 4,634,551 | 1/1987 | Burns et al. | 252/102 |
| 4,659,519 | 4/1987 | Ku | 260/502 R |
| 4,671,891 | 6/1987 | Hartman | 252/102 |
| 4,681,592 | 7/1987 | Hardy et al. | 8/11 |
| 4,686,063 | 8/1987 | Burns | 252/102 |
| 4,795,594 | 1/1989 | Dankowski | 260/502 R |

FOREIGN PATENT DOCUMENTS

| | | |
|---|---|---|
| 0325288 | 7/1989 | European Pat. Off. . |
| 0325289 | 7/1989 | European Pat. Off. . |

OTHER PUBLICATIONS

Chem. Abst. 10:8017 (1953).
Taub and Leipold, J. Chem. Eng. Data 10:399 (1965).
Hotze et al, Chemical Abstracts, vol. 78, #25, p. 386, 1973, 159273y.
Balenovic et al, Journal of the American Chemical Society, 1962, pp. 3821–3822.
Hotze et al Chemical Abstracts, vol. 78, #28, p. 386, 1973, 159273y.
Balenovic et al, Journal of the Amer. Chem. Soc, 1962, pp. 3821–3822.
Porker et al, JACS, vol. 77, 1955, 4037–41.
Taub et al, Journal of Organic Chemistry, vol. 24, 1959, pp. 2062–2063.
Balenovic et al, J Chem. Soc, 1962, pp. 3821–3822.
Porker, JACS, vol. 77, 1955, p. 4037–41.
Balenovic et al, JACS, 1962, pp. 3821–22.
Halze et al, Chem Abs, vol. 78, #28, p. 386, 1973.
Balenovic et al, *J. Chem. Soc,* 1962, pp. 3821–3822.
Taub, B. et al, J. Org. Chem. 24, 2062–2063 (1959).
Benson, R. et al., J. Am. Chem. Soc. 70, 2115–2118 (1948).
Balenovic et al, Chem. Ind., 1961, 469–470.

*Primary Examiner*—Deborah D Carr
*Attorney, Agent, or Firm*—Connolly and Hutz

[57] ABSTRACT

Imidoperoxycarboxylic acids, processes for their preparation and their use

Imidopercarboxylic acids or salts thereof of the formula

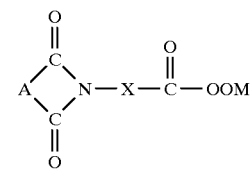

in which A denotes a group of the formula

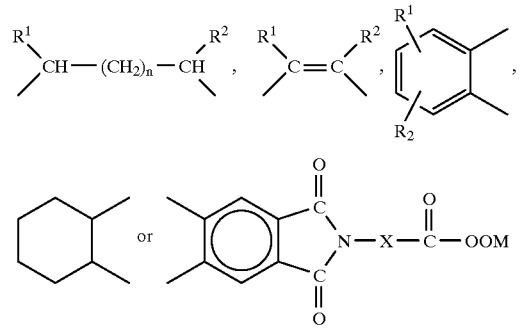

n denotes the number 0, 1 or 2,
$R^1$ denotes hydrogen, chlorine, bromine, $C_1$–$C_{20}$-alkyl, $C_2$–$C_{20}$-alkenyl, aryl, or alkylaryl,
$R^2$ denotes hydrogen, chlorine, bromine or a group of the formula —$SO_3M$, —$CO_2M$, $CO_3M$ or $OSO_3M$,
M denotes hydrogen, an alkali metal or ammonium ion or the equivalent of an alkaline earth metal ion and
X denotes $C_3$–$C_{19}$-alkylene or arylene, preferably phenylene.

These compounds are suitable as stable peroxide compounds in bleaching, oxidizing and cleaning agents.

1 Claim, No Drawings

IMIDOPEROXYCARBOXYLIC ACIDS, THEIR USE IN DETERGENTS AND CLEANING AGENTS

This application is a continuation of application Ser. No. 08/456,293 filed on May 31, 1995, now abandoned, which in turn is a continuation of Ser. No. 07/746,929, filed Aug. 19, 1991, now abandoned, which in turn is a continuation of Ser. No. 07/376,000, filed Jul. 6, 1989, now U.S. Pat. No. 5,061,807.

BACKGROUND AND PRIOR ART

Inorganic per-salts have been known for a long time as bleaching additives in detergents. However, since they only display their optimum bleaching power at temperatures above 60° C., a number of organic compounds which react with hydrogen peroxide during the washing process to release a peroxycarboxylic acid, which already has a bleaching action at 40–60° C., have been described for activation of these per-salts. A review of numerous known perborate activators, such as N-acyl compounds (tetraacetylethylenediamine, tetraacetylmethylenediamine or tetraacetylglycoluril) or activated esters (pentaacetylglucose, sodium acetoxybenzenesulfonate or sodium benzoyloxybenzenesulfonate) is given, for example, in U.S. Pat. No. 4,248,928.

In addition, a number of organic peroxycarboxylic acids have recently been described as bleaching systems for detergents. As well as peroxycarboxylic acids which are already commercially available, such as dodecanedipercarboxylic acid (EP 127,782) and monoperoxyphthalic acid (EP 27,693), persuccinic acid (DE 3,438,529), perglutaric acid (DE 3,539,036) and sulfoperbenzoic acid (EP 124,969) are described. The problem with these peroxycarboxylic acids is, however, their low storage stability, which in some cases is only guaranteed by particular physical or chemical stabilization. The preparation of magnesium salts (EP 105,689) or an addition of phosphane oxide/sodium sulfate (DE 3,320,497) has proved to be particularly appropriate here. According to EP 170,386, organic peroxycarboxylic acids are also stabilized by an additional amide group in the molecule. Examples of these are N-decanoyl-6-aminoperoxycaproic acid or 3-(N-nonyl-carbamoyl)-perpropionic acid. The storage stability of these compounds can be additionally increased by conversion into the magnesium salt and by addition of borates (U.S. Pat. No. 4,686,063). However, the free peroxycarboxylic acids described to date already exhibit a clear decrease in active oxygen under relatively mild storage conditions. As our own experiments show, this is also the case with the imidopercarboxylic acids already described in J. Chem. Soc. 1962, 3821 and Chem. Ind. 1961, 469. There thus continues to be a great interest in storage-stable organic peroxycarboxylic acids having a high bleaching efficiency which are conveniently accessible in a simple and reliable manner.

SUMMARY OF THE INVENTION

Surprisingly, it has now been found that the organic peroxycarboxylic acids described below have a considerably higher storage stability than all the amido- or imidoperoxycarboxylic acids known to date.

The invention thus relates to imidopercarboxylic acids or salts thereof of the general formula

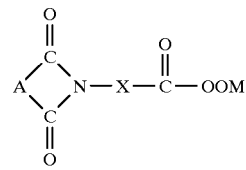

in which A denotes a group of the formula

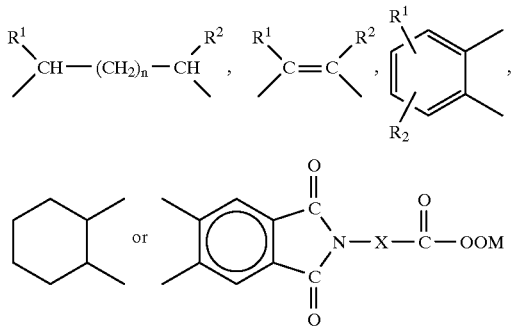

n denotes the number 0, 1 or 2,
$R^1$ denotes hydrogen, chlorine, bromine, $C_1$–$C_{20}$-alkyl, $C_2$–$C_{20}$-alkenyl, aryl, preferably phenyl, or alkylaryl, preferably $C_1$–$C_4$-alkylphenyl,
$R^2$ denotes hydrogen, chlorine, bromine or a group of the formula —$SO_3M$, —$CO_2M$, $CO_3M$ or $OSO_3M$,
M denotes hydrogen, an alkali metal or ammonium ion or the equivalent of an alkaline earth metal ion and
X denotes $C_1$–$C_{19}$-, preferably $C_3$–$C_{19}$-alkylene or arylene, preferably phenylene.

DESCRIPTION OF THE PREFERRED EMBODIMENTS

The imidopercarboxylic acids or salts thereof of the above formula in which

A denotes a group of the formula

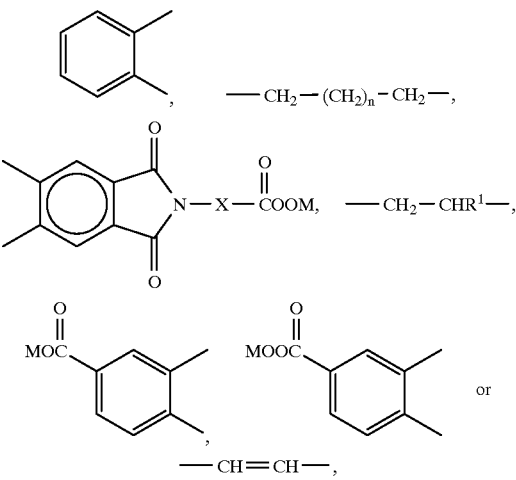

n denotes the number 0 or 1,
$R^1$ denotes $C_1$–$C_{20}$-alkyl or $C_2$–$C_{20}$-alkenyl, X denotes $C_3$–$C_{11}$-alkylene and
M denotes hydrogen, an alkali metal or ammonium ion or the equivalent of an alkaline earth metal ion, are preferred.

ω-Phthalimidoperoxyhexanoic acid, ω-2-dodecylsuccinimidoperoxyhexanoic acid, ω-phthalimidoperoxybutanoic acid and ω-trimellitimidoperoxyhexanoic acid are particularly preferred.

The imidoperoxycarboxylic acids are prepared by the steps:

-a- Synthesis of the imidocarboxylic acids
-b- Oxidation to the percarboxylic acid
-c- Isolation of the imidoperoxycarboxylic acid and if appropriate preparation of a suitable salt.

The individual steps are explained in more detail below. The preparation of the imidocarboxylic acid in step -a- can be carried out in a manner which is known per se by reaction of anhydrides of the formula

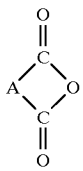

with amino acids of the formula

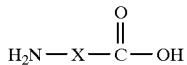

(see Houben-Weyl, Methoden der Organischen Chemie (Methods of Organic Chemistry), XI/2, page 17).

Anhydrides which can be employed are, in particular, succinic anhydride, glutaric anhydride, maleic anhydride, trimellitic anhydride, phthalic anhydride, pyromellitic anhydride and alkyl- or alkenylsuccinic anhydrides, and amino acids which can be employed are ω-aminobutyric acid, ω-aminovaleric acid, ω-aminocaproic acid and ω-aminolauric acid.

The imidocarboxylic acids can also be prepared particularly inexpensively from lactams. For this, the lactam is reacted with the anhydride in the presence of water under pressure for 2 to 20 hours, preferably 5 to 10 hours, at a temperature of 100 to 250° C., preferably 120 to 200° C., under an inert gas atmosphere in a suitable reaction vessel. The increased pressure can be 1 to 30 bar, preferably 2 to 5 bar. Lactams having a $C_3$–$C_{19}$-alkylene group, such as γ-pyrrolidone, δ-piperidone, ε-caprolactam and ω-laurolactam, are particularly preferred.

The conversion of the imidocarboxylic acids obtained in step -a- into imidopercarboxylic acids is carried out by reaction with an oxidation mixture of hydrogen peroxide and a strong acid. Hydrogen peroxide is employed as a 30 to 95 per cent strength, preferably 35 to 50 per cent strength, aqueous solution. Suitable acid catalysts in addition to sulfuric acid are methanesulfonic acid or an acid ion exchanger. Sulfuric acid is used as a 50 to 96 per cent strength, preferably 75 to 96 per cent strength, aqueous solution.

Hydrogen peroxide is used in 1 to 20 times, preferably 1.5 to 4 times, the molar excess. It has furthermore proved favorable to carry out the hydrogen peroxide addition in portions. The amount of sulfuric acid depends on the imidocarboxylic acid. A 2- to 5-fold excess—based on the imidocarboxylic acid—is in general employed. The reaction temperature depends on the stability of the peroxycarboxylic acid formed and is between 5 and 50° C., preferably between 15 and 45° C.

Since the imidoperoxycarboxylic acids claimed in most cases precipitate out of the reaction mixture, they can be isolated in step -c- in a simple manner by filtration or centrifugation. The precipitation process can be accelerated and brought to completion by addition of water. It is also possible to separate off the imidoperoxycarboxylic acids by extraction with an organic solvent. If appropriate, the imidoperoxycarboxylic acids can be converted into their salts in a manner which is known per se.

The imidoperoxycarboxylic acids according to the invention and salts thereof are solid and almost odorless, have a low vapor pressure and are of excellent thermal stability. They can be employed for bleaching, oxidation or disinfection purposes as solutions, powders or in processed form by themselves or in combination with other substances.

They are preferably employed as bleaching agents in solid or liquid detergents and cleaning agents, since their bleaching and disinfecting action is already fully effective in a wide temperature range below 60° C.

The acids or salts thereof in granular, extruded, tableted or agglomerated form are particularly suitable for incorporation into pulverulent detergents. Possible additives for this processing method are auxiliaries which are known per se, such as boric acid, sulfates, phosphates, carbonates, zeolites, carboxymethylcellulose and the like, and film-forming substances, such as fatty acids, fatty acid amides or esters, fatty alcohol polyglycol ethers or polyethylene glycols.

The compounds according to the invention prove to be effective in at least the same manner but in many cases superior to the known bleaching system of perborate/TAED (tetraacetylethylenediamine). Whereas bleaching systems based on perborate tend to fix the blood from blood stains onto the fabric and in this way drastically reduce its ease of washing out, this antagonistic effect is not observed when the peroxycarboxylic acids according to the invention which are described here are employed.

If equimolar amounts of active oxygen are used, the compounds according to the invention are equivalent in their bleaching efficiency on tea and red wine stains to the peroxycarboxylic acids and peroxy/dicarboxylic acids described to date, and in most cases are even superior. A significant oil-solubility of the compounds described here is furthermore advantageous, which means that, in particular, hydrophobic oil-containing stains, such as grilling oil or spaghetti sauce, are readily bleached.

General Instructions for the Preparation of Imidoperoxycarboxylic Acids

The imidocarboxylic acids are dissolved in 2 to 2.5 times the amount of sulfuric acid, and 2.5 equivalents of hydrogen peroxide (35–50 per cent strength) are added dropwise, while cooling with ice, so that the internal temperature can be kept between 40 and 45° C. When the addition has ended, the mixture is cooled to 25–30° C. and diluted with water and the peracid which has precipitated is filtered off with suction. The filter cake is washed with water and dried at 35° C. in a vacuum drying cabinet.

EXAMPLE 1 a) ω-Phthalimidobutanoic acid 74.05 g (0.5 mol) of phthalic anhydride, 43.55 g (0.5 mol) of γ-pyrrolidone and 9 g of water are reacted in an autoclave for 5 hours at 180° C. under 3 bar of nitrogen. The melt is then poured into a porcelain dish.

Yield: 116.2 g (99.6%), white crystals

Melting point: 110–112° C.

b) ω-Phthalimidoperoxybutanoic acid 46.6 g (0.2 mol) of ω-phthalimidobutanoic acid are oxidized in accordance with the general instructions.

Yield: 46.4 g (93%), white crystals

Active oxygen content: 6.1% (95.3%), determined by iodometric titration.

Melting point: 102–106° C.

EXAMPLE 2 a) ω-Phthalimidohexanoic acid 213.2 g (1 mol) of ε-caprolactam, 18 g of water and 148.1 g (1 mol) of phthalic anhydride are reacted in an autoclave for 5 hours at 160° C. under 3 bar of nitrogen. The melt is then poured into a porcelain dish.

Yield: 261 g (99.8%), white crystals

Melting point: 104–105° C.

b) ω-Phthalimidoperoxyhexanoic acid 653.2 g (2.5 mol) of ω-phthalimidohexanoic acid are oxidized in accordance with the general instructions.

Yield: 636.6 g (91.8%), white crystals

Active oxygen content: 5.4% (93.6%)

Melting point: 89–90° C.

EXAMPLE 3 a) ω-[2-Dodecylsuccinnimido]hexanoic acid 268.4 g (1 mol) of dodecylsuccinic anhydride, 113.2 g (1 mol) of ε-caprolactam and 18 g of water are reacted in an autoclave for 7 hours at 180° C. under a nitrogen pressure of 3 bar. The melt is then poured into a porcelain dish.

Yield: 381.2 g (99.9%), white crystals

Melting point: 74–75° C.

b) ω-[2-Dodecylsuccinimido]peroxyhexanoic acid 20 g (0.05 mol) of ω-[2-dodecylsuccinimido]hexanoic acid are oxidized in accordance with the general instructions.

Yield: 17.7 g (89%), white crystals

Active oxygen content: 3.7% (96.1%)

EXAMPLE 4 a) ω-[4-Carboxyphthalimido]hexanoic acid 191.1 g (1 mol) of trimellitic anhydride, 113.1 g (1 mol) of ε-caprolactam and 18 g of water are reacted in an autoclave for 5 hours at 210° C. under a nitrogen pressure of 3 bar. The melt is then poured into a porcelain dish.

Yield: 304.1 g (100%), white crystals

Melting point: 196–197° C.

b) ω-[4-Carboxyphthalimido]peroxyhexanoic acid 244.2 g (0.8 mol) of ω-[4-carboxyphthalimido]hexanoic acid are oxidized in accordance with the general instructions.

Yield: 235 g (87%)

Active oxygen content: 4.8% (96%)

Melting point: 144° C.

EXAMPLE 5 a) Pyromellitimido-di-ω-hexanoic acid 76 g (0.35 mol) of pyromellitic anhydride and 79.2 g (0.7 mol) of ε-caprolactam are reacted with 11 g of water for 18 hours at 250° C. under a nitrogen pressure of 4 bar in an autoclave. The melt is then poured into a porcelain dish.

Yield: 149 g (96%), white crystals

Melting point: 222–225° C.

b) Pyromellitimido-di-ω-peroxyhexanoic acid 10 g (0.023 mol) of pyromellitimido-di-ω-hexanoic acid are reacted with five equivalents of hydrogen peroxide in accordance with the general instructions.

Yield: 9 g (82%), white crystals

Active oxygen content: 6.6% (98.5%)

Melting point: 139° C.

EXAMPLE 6 a) ω-Phthalimidobutanoic acid 74.05 g (0.5 mol) of phthalic anhydride and 51.55 g (0.5 mol) of ω-aminobutyric acid are heated at 170–180° C. under a nitrogen atmosphere. During this procedure, the water of reaction formed is distilled off completely, and the melt is then poured into a porcelain dish.

Yield: 116.2 g (99.6%), white crystals

Melting point: 110–112° C. (literature: 117–118° C.)

b) ω-Phthalimidoperoxybutanoic acid 18 g (0.077 mol) of ω-phthalimidobutanoic acid are oxidized in accordance with the general instructions.

Yield: 18 g (93.8%), white crystals

Active oxygen content: 6.0% (93.6%), determined by iodometric titration

Melting point: 106–109° C.

EXAMPLE 7 a) ω-Phthalimidohexanoic acid 213.2 g (1 mol) of ε-caprolactam, 148.1 g (1 mol) of phthalic anhydride and 2 g of water are reacted in an autoclave for 10 hours at 180° C. under 3 bar of nitrogen. The melt is then poured into a porcelain dish.

Yield: 261 g (99.8%), white crystals

Melting point: 104–105° C. (literature: 106° C.)

b) ω-Phthalimidoperoxyhexanoic acid 174 g (0.67 mol) of ω-phthalimidohexanoic acid are oxidized in accordance with the general instructions.

Yield: 165 g (89%), white crystals

Active oxygen content: 5.6% (97%)

Melting point: 90° C.

EXAMPLE 8 a) ω-Succinimidohexanoic acid 100.1 g (1 mol) of succinic anhydride are reacted with 113.2 g (1 mol) of ε-caprolactam in the presence of 2 g of water in an autoclave for 10 hours at 180° C. under 3 bar of nitrogen.

Yield: 213.2 g (100%), white crystals

Melting point: 76–77° C.

b) ω-Succinimidoperoxyhexanoic acid 20 g (0.094 mol) of ω-succinimidohexanoic acid in 50 g of sulfuric acid (96 per cent strength) are oxidized in accordance with the general instructions.

Yield: 18.3 g (84.9%), white crystals
Active oxygen content: 5.3% (76.0%)

EXAMPLE 9 a) ω-[2-Dodecylsuccinimido]hexanoic acid 268.4 g (1 mol) of dodecylsuccinic anhydride, 113.2 g (1 mol) of caprolactam and 2 g of water are reacted and the product is isolated, analogously to Example 5.

Yield: 381.2 g (99.9%), white crystals
Melting point: 74–75° C.

b) ω-[2-Dodecylsuccinimido]peroxyhexanoic acid 20 g (0.05 mol) of ω-[2-dodecylsuccinimido]hexanoic acid in 50 g of sulfuric acid (96% strength) are oxidized in accordance with the general instructions.

Yield: 17.7 g (89%)
Active oxygen content: 3.7% (96.1%)

EXAMPLE 10 a) Pyromellitimido-di-ε-caproic acid 76 g of pyromellitic anhydride (0.35 mol) and 79.2 g of caprolactam (0.7 mol) are kept in an autoclave with 2 g of water for 18 hours at 250° C. under a nitrogen pressure of 4 bar. Thereafter, the autoclave is opened at this temperature and the melt is poured into a porcelain dish.

Melting point: 232° C.
Yield: 149 g (96%), white crystals b) Pyromellitimido-di-ε-percaproic acid 10 g of pyromellit-imido-di-ε-caproic acid (0.023 mol) were oxidized an accordance with the general instructions.

Melting point: 139° C.
Yield: 9 g (82%)
Active oxygen content: 6.6% (98.5%)

EXAMPLE 11

Washing Experiments in a Launder-O-Meter

The experiments were carried out at 40 and 60° C. in a Launder-O-Meter using test stains of tea on WFK cotton, red wine on EMPA cotton and standard stain on WFK cotton. The bleaching systems were metered so that in each case 25 mg/l of active oxygen resulted in the wash liquor. In each case 1.5 g/l of IEC detergent was employed as the detergent. The washing time was 30 minutes. The bleaching action was determined as the increase in reflectance on the various test fabrics. The evaluation is carried out in the usual manner.

| Bleaching system | Reflectance values | | | | | |
|---|---|---|---|---|---|---|
| | Standard | | Tea | | Red wine | |
| | 40° C. | 60° C. | 40° C. | 60° C. | 40° C. | 60° C. |
| Perborate | 49.5 | 59.4 | 58.4 | 62.8 | 55.5 | 56.9 |
| Perborate/TAED | 48.3 | 63.6 | 66.9 | 67.4 | 59.8 | 60.0 |
| PAP | 49.0 | 64.9 | 72.2 | 75.0 | 67.7 | 73.1 |

The results show a significantly better bleaching performance by the peracid PAP (ω-phthalimidoperoxyhexanoic acid) according to the invention in comparison with the previously customary bleaching system of perborate/TAED (tetraacetylethylenediamine) when equimolar amounts of the bleaching system are employed.

EXAMPLE 12

Washing Experiments in a Launder-O-Meter

The experiments were carried out analogously to Example 5. The peroxycarboxylic acids DPDDA (diperoxydodecanedioic acid), PMP (monoperphthalic acid) and NAPSA (nonylmonoamidopersuccinic acid) were tested against PAP as the bleaching systems.

| Peroxy acids | Reflectance values | | | |
|---|---|---|---|---|
| | Tea | | Red wine | |
| | 38° C. | 60° C. | 38° C. | 60° C. |
| DPDDA | 69.6 | 73.6 | 65.5 | 71.8 |
| PMP | 66.8 | 71.1 | 61.1 | 65.4 |
| NAPSA | 68.1 | 72.2 | 63.7 | 68.6 |
| PAP | 68.4 | 77.1 | 67.2 | 74.3 |

EXAMPLE 13

Washing Experiments in a Washing Machine

The experiments were carried out in a Miele washing machine (Automatic W432) with the 40° temperature program (main wash and stepwise spinning) using 2 kg of ballast.

The bleaching action was measured as the increase in reflectance on EMPA test strips (EMPA 103). In each case 4.5 g/l of detergent prepared by mixing IEC detergent with the particular bleaching system were employed.

| Detergent | Standard | Red wine | Blood |
|---|---|---|---|
| IEC | 24.7 | 54.8 | 65.5 |
| IEC/10% of perborate | 27.8 | 54.9 | 37.1 |
| IEC/10% of perborate/3% of TAED | 28.0 | 57.7 | 44.2 |
| IEC/3% of PAP | 32.2 | 57.8 | 68.5 |
| IEC/6% of PAP | 34.9 | 63.1 | 66.6 |
| IEC/9% of PAP | 34.4 | 66.6 | 65.5 |
| IEC/6% of DSIPH | 36.6 | 59.1 | 65.6 |

TAED=tetraacetylethylenediamine
PAP=ω-phthalimidoperoxyhexanoic acid
DSIPH=ω-[2-dodecylsuccinimido]peroxyhexanoic acid The experiments show a significant superiority of the imidoperoxycarboxylic acids according to the invention over known bleaching systems. In particular, no antagonistic effect on the ease of washing out of blood stains are observed when the peracids are used.

EXAMPLE 14

Determination of the Oil-Solubility of Bleaching Systems

To determine the oil-solubility of a bleaching system, the bleaching system was introduced into a mixture of 50% of demineralized water and 50% of isopropyl myristate at 20° C., the pH was brought to 9 and the mixture was stirred intensively for 10 minutes. After separation of the phases, the peroxycarboxylic acid content in the oil and water phases was determined by titrimetry.

| Bleaching system | Oil solubility at pH 9 |
|---|---|
| Perborate/TAED | 6% |
| DPDDA | 15% |
| PAP | 38% |
| Perborate/isonobs | 54% |
| DSIPH | 86% |

EXAMPLE 15

Storage Experiments on the Free Peroxycarboxylic Acids

The experiments were carried out in open vessels in a heating cabinet. The content of peroxycarboxylic acid was determined by titrimetry.

| Peroxycarboxylic acid | Storage time (weeks) | Temperature | Loss of active oxygen |
|---|---|---|---|
| PAP | 4 | 25° C. | 1.4% |
| NAPSA | 4 | 25° C. | 14.6% |
| PAP | 4 | 40° C. | 2.0% |
| NAPSA | 4 | 40° C. | 29.3% |
| PAP | 4 | 50° C. | 12.0% |
| NAPSA | 2 | 50° C. | 100.0% |

We claim:

1. A detergent or cleaning agent comprising omega-phthalimidoperoxyhexanoic acid prepared by reacting phthalic acid or phthalic anhydride with caprolactam in the presence of water and under a pressure of 2–30 bar to form an imidocarboxylic acid, and oxidizing the imidocarboxylic acid with hydrogen peroxide in the presence of a strong acid.

* * * * *